(12) United States Patent
Benje

(10) Patent No.: US 7,001,573 B1
(45) Date of Patent: Feb. 21, 2006

(54) PROCESS FOR REMOVING FINE DUST FROM A FLUIDIZED-BED REACTOR, IN PARTICULAR FOR THE OXYCHLORINATION OF ETHYLENE

(75) Inventor: Michael Benje, Darmstadt (DE)

(73) Assignee: UHDE GmbH, Dortmund (DE)

( * ) Notice: Subject to any disclaimer, the term of this patent is extended or adjusted under 35 U.S.C. 154(b) by 0 days.

(21) Appl. No.: 09/379,481

(22) Filed: Aug. 23, 1999

(30) Foreign Application Priority Data

Aug. 21, 1998 (DE) .................... 198 37 957

(51) Int. Cl.
B01J 8/24 (2006.01)
C07C 17/156 (2006.01)
C07C 17/38 (2006.01)

(52) U.S. Cl. .............. 422/147; 422/139; 422/211; 422/212; 422/213; 570/243; 570/224

(58) Field of Classification Search ............ 422/147, 422/144, 143, 142, 140.41, 188–190, 194, 422/211, 212; 55/350.1, 341.1–341.7, 312, 55/484, 482; 95/278–80; 96/399, 417, 407, 96/408, 411; 570/243, 224
See application file for complete search history.

(56) References Cited

U.S. PATENT DOCUMENTS

| | | | | |
|---|---|---|---|---|
| 2,548,875 A | * | 4/1951 | Degnen et al. .............. 202/254 |
| 2,585,274 A | * | 2/1952 | Reichl ........................ 422/143 |
| 3,296,319 A | * | 1/1967 | Bohl et al. .................. 570/224 |
| 3,513,638 A | * | 5/1970 | Young et al. ................. 55/302 |
| 3,615,256 A | * | 10/1971 | Miller et al. ................ 422/146 |
| 3,907,912 A | * | 9/1975 | Antonini et al. ............ 570/243 |
| 4,226,798 A | * | 10/1980 | Cowfer et al. ................. 137/4 |
| 4,243,650 A | * | 1/1981 | Tsao ........................ 423/210.5 |
| 4,306,888 A | * | 12/1981 | Cheng ......................... 55/291 |
| 4,310,713 A | * | 1/1982 | Legutke et al. ............. 570/243 |
| 4,328,353 A | * | 5/1982 | Shah .......................... 556/465 |
| 4,973,458 A | * | 11/1990 | Newby et al. ........ 423/244.07 |
| 5,143,530 A | * | 9/1992 | Haldipur et al. .............. 55/302 |
| 5,198,397 A | * | 3/1993 | Raterman ................... 208/113 |
| 5,314,616 A | * | 5/1994 | Smith ........................ 184/6.24 |
| 5,435,972 A | * | 7/1995 | Daw et al. .................. 422/108 |

FOREIGN PATENT DOCUMENTS

DE 19546068 A1 * 6/1997
DE 19753165 A1 * 6/1999

* cited by examiner

*Primary Examiner*—Hien Tran
*Assistant Examiner*—Jennifer Leung
(74) *Attorney, Agent, or Firm*—Katten Muchin Roseman LLP

(57) ABSTRACT

By a process for removing fine dust from a fluidized-bed reactor, in particular for the oxychlorination of ethylene, is intended to permit specific control of the amount of fine dust particles in a reactor while reducing the height of the reactor and the same time filtering off the fine dust from the main stream leading to the quench. This is achieved if the fine dust inside, the reactor is removed via filter cartridges, and the reaction gas mixture is passed to the quench from the reactor dome, a part-stream in the form of a bypass stream having a predetermined fine dust fraction below a predetermined particle size being removed from the reactor in addition to the main stream.

6 Claims, 2 Drawing Sheets

PROCESS FOR REMOVING FINE DUST FROM A FLUIDIZED-BED REACTOR, IN PARTICULAR FOR THE OXYCHLORINATION OF ETHYLENE

FIELD OF THE INVENTION

The invention relates to a process for removing fine dust from a fluidized-bed reactor, in particular for the oxychlorination of ethylene.

BACKGROUND OF THE INVENTION

There is a number of known processes in which chemical reactions are initiated by means of catalysts in a fluidized bed, for example in oxychlorination, in which ethylene-oxygen and HCl are reacted in a fluidized-bed reactor over a copper-containing catalyst to give 1,2-dichloroethane and water.

In such fluidized-bed processes, abrasion of the fluidized-bed particles inevitably occurs, resulting in fine dust in the fluidized bed. Since these fine dust particles are entrained by the reaction gas mixture, they can be separated off inside or outside the reactor, for example by cyclones connected in series or by fine dust filters, for example by hoses of a Gore-Tex membrane on PTFE needle felt.

German Laid-open Specification 20 19 210 and also DE-40 30 086-C1 disclose fluidized-bed reactors and fluidized-bed processes, respectively, comprising filter cartridges, arranged inside the reactor, for the exit gas. Such filter cartridges invariably allow small amounts of fine dust to pass through (cf. expert opinion DE-21 66 912-A1, in particular the last paragraph of the description of this publication).

Owing to the physical circumstances of the fluidized beds used, cyclone inlets must be arranged at a certain minimum height above the fluidized bed since from this height onward the dust content in the gas taken off is approximately constant, and about 25% of the height of the reactor may be stated as an example without the invention being restricted to these dimensions.

It is known that efforts have been made to replace the cyclones and the downstream fine dust filters with a single fine dust filter arranged directly in the reactor, it being possible to clean the filter cartridges used by means of compressed gas pulses from the series side. The filters which are used may dip directly into the fluidized bed, which can inevitably lead to a reduction in the height of reactors. Furthermore, such a procedure should permit complete dust separation.

A particular disadvantage of this procedure is, however, that fine dust fractions which inevitably differ considerably from the desired spherical shape of the fluidized-bed particles inevitably accumulate in the fluidized bed, so that the characteristics of the fluidized bed change. While a very small amount is useful for better fluidization of the fluidized bed, larger amounts can lead to a transition from an effervescent fluidized bed to a percussive fluidized bed or to coating of the cooling surfaces, which leads to a gradual deterioration and finally to the collapse of heat transfer.

SUMMARY OF THE INVENTION

It is here that the present invention is of use, its object being to permit specific control of the amount of fine dust particles in a reactor while reducing the height of the reactor and at the same time filtering off the fine dust from the main stream leading to the quench.

This object according to the invention is achieved by a process of the type defined at the outset if the fine dust inside the reactor is removed via filter cartridges, in particular sintered metal filter cartridges, having a defined larger pore size than those of the fine dust filter, and the reaction gas mixture is passed to the quench from the reactor dome, it being possible in a further embodiment to ensure that a part-stream in the form of a bypass stream having a predetermined fine dust fraction below a predetermined particle size is removed from the reactor in addition to the main stream.

By means of the procedure according to the invention, it is possible to establish exactly the desired fine dust fraction in the fluidized-bed reactor. If, for example by sieve analysis of a catalyst sample, it is found that the fine dust fraction in the reactor increases above a predeterminable, permissible level, the bypass line and the coordinated filter cartridges can be opened and fine dust fractions below a specific minimum particle size thus gradually leave the reactor.

In a further embodiment, it is envisaged that the main stream and the bypass stream are removed from separate dome spaces of the reactor, it being possible, instead of separate dome spaces, also to provide groups of filter baseplates having filter cartridges, which are then controlled in different ways.

The bypass stream can be switched on and off on the basis of different criteria, for example on the basis of a corresponding, already mentioned analysis of a catalyst sample, on the basis of the change in the heat transfer or the deterioration of the fluidization behavior of the fluidized bed, for example if an abnormal high density of the fluidized bed is found.

To achieve the object set, the invention also provides a fluidized-bed reactor, in particular for the oxychlorination of ethylene, with the use of catalyst granules subjected to abrasion, e.g. γ-alumina having a mean particle size of from about 40 to 60 μm, which is distinguished by the fact that at least one baseplate having filter cartridges, in particular sintered metal filter cartridges, is provided in the dome of the reactor, it being possible for the filter cartridges to dip into the upper region of the fluidized bed.

At this point, it may be noted that the filter cartridges may consist of another material, e.g. ceramic, and in this respect the invention is not restricted to said sintered metal filter cartridges.

An embodiment provides a fluidized-bed reactor which is distinguished by the fact that the dome space is divided, above the plate carrying the filter cartridges on its lower surface, into at least two chambers, each having an outlet for a main stream to the quench and a bypass stream.

The division of the plate carrying the filter cartridges into two regions which are separated from one another in the dome space has the advantage that the bypass stream can be switched on and off separately without greatly influencing the other filters.

Instead of such a division, the filter cartridges may also be grouped together in bundles, combined and inserted from the outside into the dome space and flange-mounted there. Such a bundle can then be switched, for example, as a bypass.

The invention also envisages that the filter elements coordinated with the bypass have a pore size differing from that of the fine dust filter cartridges, for the controlled passage of fine dust fractions.

The ratio of filter elements allowing through fine dust to filter elements retaining fine dust may be in the region of 1:9, but the invention is not restricted to these numbers and other ratios may also be provided here.

The plate or plates carrying the filter cartridges can be provided with a cleaning means by means of compressed gas pulses.

The invention is illustrated in more detail below with reference to the drawing by way of example.

DETAILED DESCRIPTION OF THE INVENTION

Figure 1:
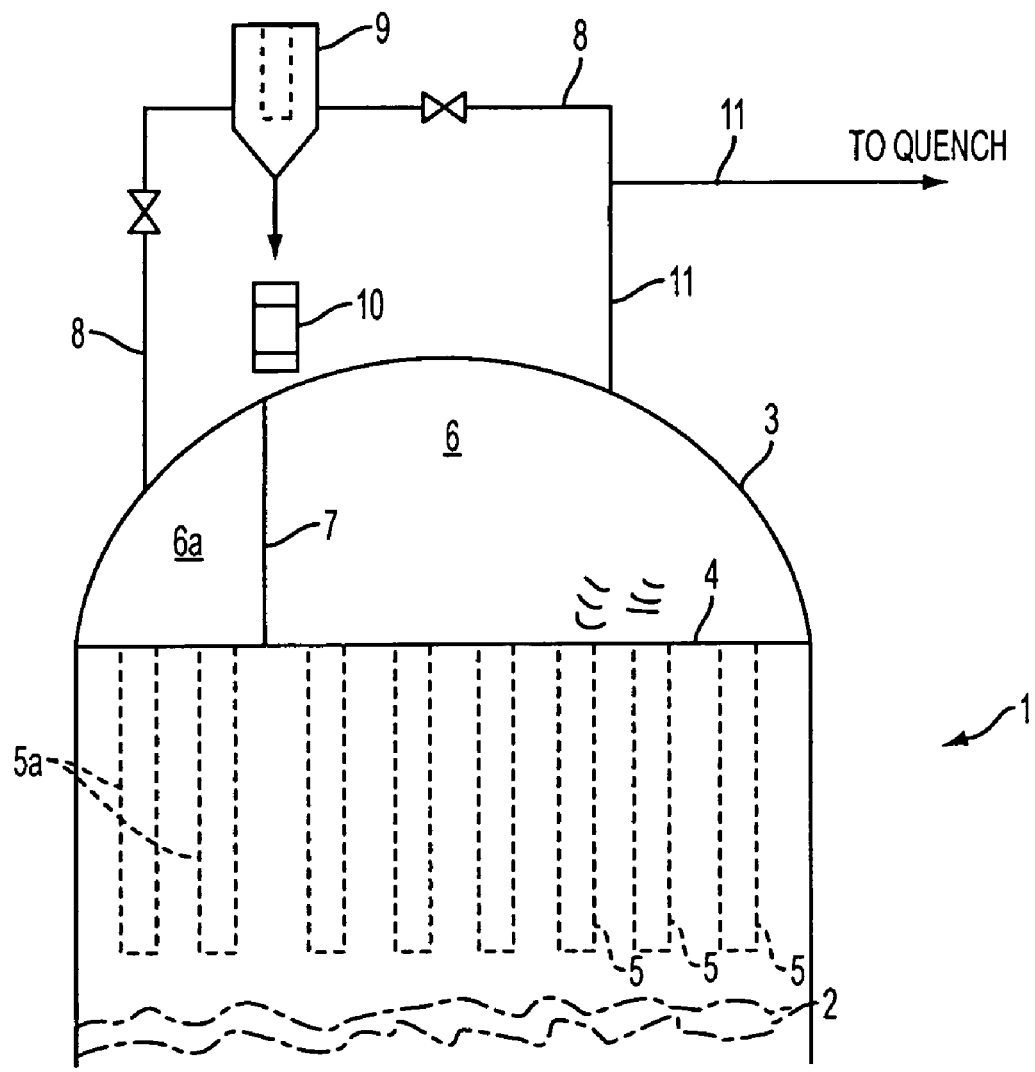
FIGS. 1 and 2 of the drawing show greatly simplified sections of reactor dome spaces with variants of the coordination, according to the invention, of filter cartridges.

A reactor, reproduced only in simplified form in the Figure and denoted generally by 1, has a fluidized bed 2 which is indicated in FIG. 1 only by its upper limit and in which, for example, γ-alumina particles having a mean particle size of from 40 to 60 μm are present, in order to react ethylene-oxygen and HCl to give 1,2-dichloroethane and water.

In the example of FIG. 1, the fluidized-bed reactor 1 has, in its dome denoted by 3, a dome plate 4 or baseplate which carries a multiplicity of filter cartridges 5 which point toward the fluidized bed 2 and, depending on the design, can optionally also dip into the fluidized bed 2.

In the example of FIG. 1, the dome space denoted by 6 is separated by a partition 7 into a larger region and a smaller region 6a, a small number of filter cartridges 5a which, in contrast to the filter cartridges 5, have pore sizes which permit discharge of fine dust being coordinated with the region 6a.

A corresponding gas stream comprising fine dust particles is fed via a bypass line 8 or bypass stream, for example to an external fine dust filter 9, and the fine dust can then be discharged and disposed of, which is indicated by a container 10, and the gas can then be fed via the bypass line 8 back to the main stream, denoted by 11.

Figure 2:
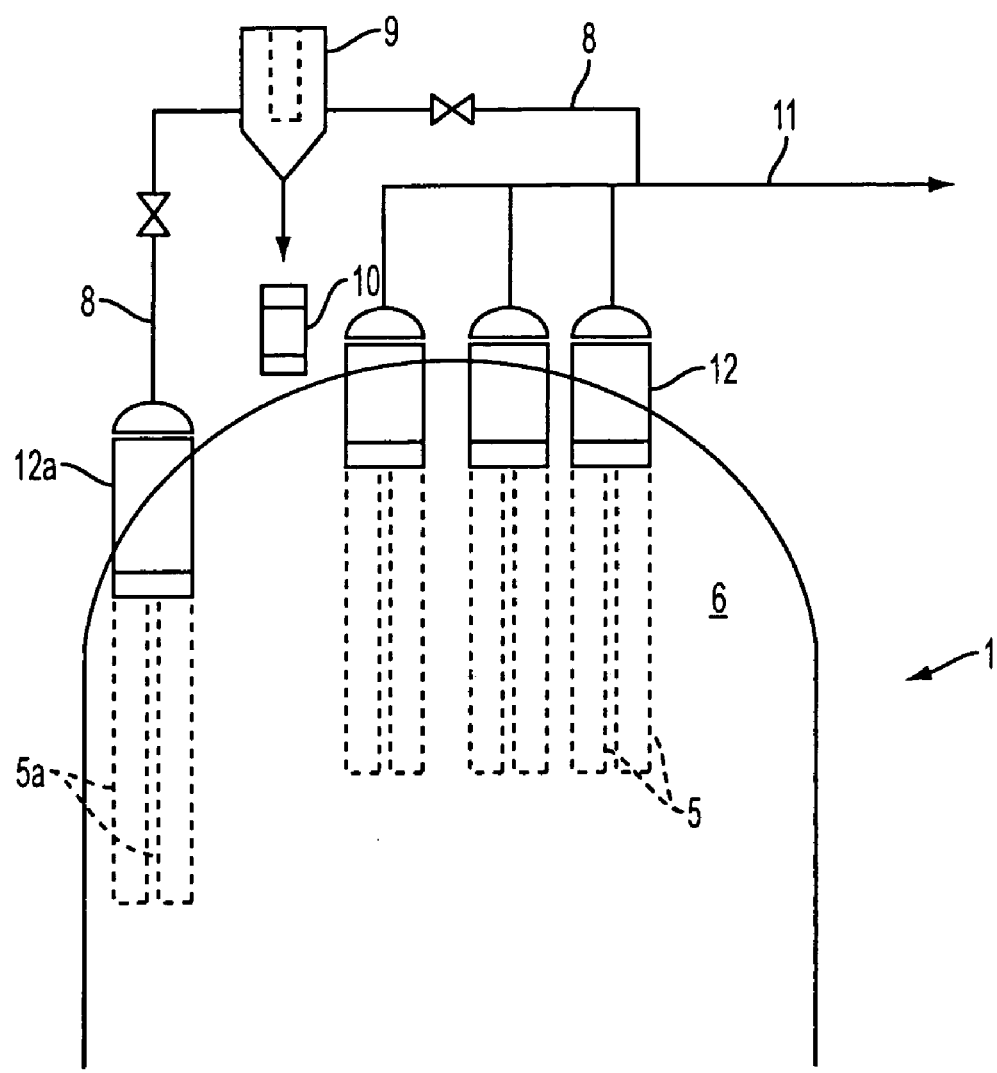

FIG. 2 shows a variant; here, groups of filter elements 12 are inserted from outside into the dome space 6, and a secondary group denoted by 12a is coordinated with the bypass line. The essentially identical parts in FIG. 2 bear the same reference symbols as in the embodiment according to FIG. 1, unless there are special features.

Here, too, the filter cartridges 5a may once again have a pore size sufficiently large for fine dust to be removed from the dome space 6 via the bypass line 8; here, as in the embodiment of FIG. 1, separation is effected via an external fine dust filter 9.

Of course, the embodiments of the invention which are described can also be modified in various respects without departing from the basic concepts; for example, a combination of the designs according to FIGS. 1 and 2 can be implemented, etc.

What is claimed is:

1. A fluidized-bed reactor for the oxychlorination of ethylene using a fluidized bed of catalyst granules subjected to abrasion, resulting in the creation of dust particles, said reactor comprising:
    a dome part defining a dome space;
    a baseplate located in said dome part of the reactor; and
    a plurality of filter cartridges carried on the lower surface of said baseplate, said filter cartridges dipping into an upper region of the fluidized bed of catalyst granules;
    wherein said dome space is divided above said baseplate into at least two chambers, said at least two chambers comprising a first chamber having an outlet for a main gas stream and a second chamber having an outlet for a bypass gas stream, wherein the bypass gas stream is connected to the main gas stream, and the main gas stream is connected to a quench vessel;
    wherein a first group of said filter cartridges is coordinated with said first chamber and in communication with the main gas stream, and a second group of said filter cartridges is coordinated with said second chamber and in communication with the bypass gas stream; and
    wherein said first group of filter cartridges have a pore size differing from a pore size of said second group of filter cartridges, said first group having a pore size configured to retain dust particles in the reactor, and said second group having a pore size configured to permit the discharge of dust particles from the reactor.

2. The fluidized-bed reactor of claim 1, wherein the ratio of the number of filter cartridges in said second group to the number of filter cartridges in said first group is approximately 1:9.

3. The fluidized-bed reactor of claim 1, wherein said baseplate is provided with a cleaning means using compressed gas pulses.

4. The fluidized-bed reactor of claim 1, wherein the filter cartridges comprise sintered metal filter cartridges.

5. A method of removing dust particles, resulting from the abrasion of catalyst granules, from a reaction gas mixture generated in the oxychlorination of ethylene in a fluidized-bed reactor, said reactor comprising a dome part divided into two separate dome spaces and a plurality of sintered metal filter cartridges communicating with each of said dome spaces, said method of comprising the steps of:
    filtering out dust particles from the reaction gas mixture using a first group of the sintered metal filter cartridges, passing the filtered reaction gas mixture to a first dome space of two separate dome spaces, and removing the filtered reaction gas mixture from the first dome space via an outlet to a main gas stream, wherein the first group of sintered metal filter cartridges is configured to retain dust particles in the reactor;
    filtering out dust particles from the reaction gas mixture using a second group of the sintered metal filter cartridges, passing the filtered reaction gas mixture to the second dome space, and removing the filtered reaction gas mixture from the second dome space via an outlet to a bypass gas stream, wherein the second group of sintered metal filter cartridges is configured to produce a filtered reaction gas mixture containing a predetermined content of dust particles of a size which is smaller than a predetermined particle size; and
    passing the contents of the main gas stream and the bypass gas stream to a quench vessel.

6. The method of claim 5, further comprising the steps of:
    analyzing a catalyst sample from the reactor;
    analyzing a change in heat transfer in the reactor;
    analyzing a deterioration of the fluidization behavior in the reactor; and
    switching on or switching off the bypass gas stream according to said analyzing steps.

\* \* \* \* \*